(12) United States Patent
Mangat et al.

(10) Patent No.: US 8,185,176 B2
(45) Date of Patent: May 22, 2012

(54) METHOD AND APPARATUS FOR VASCULATURE VISUALIZATION WITH APPLICATIONS IN NEUROSURGERY AND NEUROLOGY

(75) Inventors: Gurpreet Mangat, Markham (CA); Lukasz Brzozowski, Toronto (CA); Richard L. Croft, Oakville (CA)

(73) Assignee: Novadaq Technologies, Inc., Mississauga (CA)

( * ) Notice: Subject to any disclaimer, the term of this patent is extended or adjusted under 35 U.S.C. 154(b) by 770 days.

(21) Appl. No.: 11/912,878

(22) PCT Filed: Apr. 26, 2006

(86) PCT No.: PCT/US2006/016101
§ 371 (c)(1),
(2), (4) Date: Jun. 10, 2008

(87) PCT Pub. No.: WO2006/116634
PCT Pub. Date: Nov. 2, 2006

(65) Prior Publication Data
US 2009/0203994 A1    Aug. 13, 2009

Related U.S. Application Data

(60) Provisional application No. 60/674,890, filed on Apr. 26, 2005.

(51) Int. Cl.
*A61B 5/00* (2006.01)
(52) U.S. Cl. .................................. 600/310; 382/130
(58) Field of Classification Search .................. 600/310
See application file for complete search history.

(56) References Cited

U.S. PATENT DOCUMENTS

| | | | |
|---|---|---|---|
| 5,438,989 A | | 8/1995 | Hochman et al. |
| 5,465,718 A | | 11/1995 | Hochman et al. |
| 5,514,127 A | * | 5/1996 | Shanks .......................... 606/10 |
| 5,623,930 A | * | 4/1997 | Wright et al. ................. 600/456 |
| 5,627,907 A | * | 5/1997 | Gur et al. ...................... 382/132 |
| 5,664,574 A | * | 9/1997 | Chance .......................... 600/473 |
| 5,673,701 A | * | 10/1997 | Chance ........................ 600/473 |
| 5,689,241 A | * | 11/1997 | Clarke et al. ................. 340/575 |
| 5,699,798 A | * | 12/1997 | Hochman et al. ............ 600/420 |
| 5,803,914 A | * | 9/1998 | Ryals et al. .................. 600/407 |
| 6,074,627 A | * | 6/2000 | Dean et al. .................. 424/1.69 |
| 6,149,671 A | | 11/2000 | Nordquist et al. |
| 6,196,226 B1 | | 3/2001 | Hochman et al. |
| 6,211,953 B1 | * | 4/2001 | Niino et al. ................... 356/246 |
| 6,223,069 B1 | * | 4/2001 | Pfeiffer et al. ............... 600/431 |
| 6,233,480 B1 | | 5/2001 | Hochman et al. |
| 6,241,672 B1 | | 6/2001 | Hochman et al. |
| 6,319,273 B1 | * | 11/2001 | Chen et al. .................... 607/88 |
| 6,335,429 B1 | | 1/2002 | Cai et al. |
| 6,351,663 B1 | | 2/2002 | Flower et al. |

(Continued)

FOREIGN PATENT DOCUMENTS

JP        3896176       12/1997

(Continued)

OTHER PUBLICATIONS

Dan et al., "1% Lymphazurin vs 10% Fluorescein for Sentinel Node Mapping in Colorectal Tumors," Arch Surg, 139:1180-1184, (2004).

(Continued)

*Primary Examiner* — Sath V Perungavoor
(74) *Attorney, Agent, or Firm* — Rissman Hendricks & Oliverio, LLP

(57) ABSTRACT

The invention provides methods and systems for neurovascular imaging (150).

64 Claims, 3 Drawing Sheets

U.S. PATENT DOCUMENTS

| | | | |
|---|---|---|---|
| 6,804,549 B2 * | 10/2004 | Hayashi | 600/431 |
| 6,821,946 B2 | 11/2004 | Goldsaink et al. | |
| 6,840,933 B1 * | 1/2005 | Pang et al. | 606/4 |
| 6,853,857 B2 | 2/2005 | Pfeiffer et al. | |
| 6,899,675 B2 | 5/2005 | Cline et al. | |
| 6,915,154 B1 * | 7/2005 | Docherty et al. | 600/431 |
| 7,364,574 B2 * | 4/2008 | Flower | 606/4 |
| 7,400,755 B2 * | 7/2008 | West et al. | 382/128 |
| 7,885,438 B2 * | 2/2011 | Uppaluri et al. | 382/128 |
| 2002/0181752 A1 * | 12/2002 | Wallo et al. | 382/130 |
| 2003/0156252 A1 | 8/2003 | Morris | |
| 2003/0187349 A1 | 10/2003 | Kaneko et al. | |
| 2003/0232016 A1 | 12/2003 | Heinrich | |
| 2004/0109231 A1 | 6/2004 | Haisch et al. | |
| 2004/0156782 A1 | 8/2004 | Alam et al. | |
| 2005/0069525 A1 | 3/2005 | Mikael | |
| 2005/0107380 A1 | 5/2005 | Nimmo et al. | |
| 2005/0182321 A1 | 8/2005 | Frangioni et al. | |
| 2005/0182434 A1 * | 8/2005 | Docherty et al. | 606/170 |
| 2005/0197583 A1 | 9/2005 | Chance | |
| 2006/0108509 A1 | 5/2006 | Frangioni et al. | |
| 2006/0239921 A1 * | 10/2006 | Mangat et al. | 424/9.6 |
| 2006/0241499 A1 | 10/2006 | Irion et al. | |
| 2007/0203413 A1 | 8/2007 | Frangioni | |
| 2008/0071176 A1 * | 3/2008 | Docherty et al. | 600/476 |

FOREIGN PATENT DOCUMENTS

| | | | |
|---|---|---|---|
| WO | WO 93/25141 | | 12/1993 |
| WO | WO 01/22870 | * | 4/2001 |

OTHER PUBLICATIONS

Degrand et al., "An Operational Near-Infrared Fluorescence Imaging System Prototype for Large Animal Surgery," Technology in Cancer Research & Treatment, 2(6)1-10, (2003).

Demos, "Near-infrared autofluorescence imaging for detection of cancer," Journal of Biomedical Optics, 9(3):587-592, (2004).

Dietz et al., "Indocyanine Green, Evidence of Neurotoxicity in Spinal Root Axons," Anesthesiology, 98(2):516-520, (2003).

Frangioni "In vivo near-infrared fluorescence imaging," Current Opinion in Chemical Biology, 7:626-634, (2003).

Haglund at al., "Enhanced Optical Imaging of Rat Gliomas and Tumor Margins," Congress of Neurological Surgeons, 35(5):930-941, (1994).

Herts. "Imaging for renal tumors," Current Opin Urol, 13:181-186, (2003).

Humblet et al., "High-affinity Near-infrared Fluorescent Small-molecule Contrast Agents for In Vivo Imaging of Prostate-specific Membrane Antigen," Molecular Imaging, 4(4):448-462, (2005).

Kamolz et al., "Indocyanine green video angiographies help to identify burns requiring operation," Burns, 29:785-791, (2003).

Kim et al., "Near-infrared fluorescent type II quantum dots for sentinel lymph node mapping," Nature Biotechnology, 22(1):93-97, (2004).

Liedberg et al., "Intraoperative Sentinel Node Detection Improves Nodal Staging in Invasive Bladder Cancer," The Journal of Urology, 175:84-89, (2006).

Liedberg et al., Sentinel-Node-Diagnostik beim invasiven (Bladder Cancer and the Sentinel Node Concept), Aktuel Urol, 34:115-118, (2003).

Malmstrom at al., "Early Metastatic Progression of Bladder Carcinoma: Molecular Profile of Primary Tumor and Sentinel Lymph Node," The Journal of Urology, 168:2240-2244, (2002).

Marangos et al "In vivo visualization of the cchlear nere and nuclei with fluorescent axonal tracers," Hearing Research, 162:48-52, (2001).

Motomura et al. "Sentinel Node Biopsy Guided by Indocyanine Green Dye in Breast Cancer Patients," Jpn J Clin Oncol, 29(12):604-607, (1999).

Nakayama et al., "Functional Near-Infrared Fluorescence Imaging for Cardiac Surgery and Targeted Gene Therapy," Molecular Imaging, 1(1):365-377, (2002).

Nimura et al., "Infrared ray electronic endoscopy combined with indocyanine green injection for detection of sentinel nodes of patients with gastric cancer," British Journal of Surgery, 91:575-579, (2004).

Paques et al., "Axon-Tracing Properties of Indocyanine Green," Arch Ophthalmol, 121:367-370, (2003).

Parungo et al., "Intraoperative identification of esophageal sentinel lymph nodes with near-infrared fluorescence imaging," The Journal of Thoracic and Cardiovascular Surgery, 129(4):844-850, (2005).

Raabe et al., "Near-Infrared Indocyanine Green Video Angiography: A New Method for Intraoperative Assessment of Vascular Flow," Neurosurgery, 52(1):132-139, (2003).

Ross et al., "The ability of lymphoscintigraphy to direct sentinel node biopsy in the clinically NO neck for patients with head and neck squamous cell carcinoma," The British Journal of Radiology, 75:950-958, (2002).

Rubben et al., "Infrared Videoangiofluorography of the Skin with Indocyanine Green-Rat Random Cutaneous Flap Model and Results in Man," Microvascular Research, 47:240-251, (1994).

Schneider et al., "Fluorescence of Testicle, an Indication of Viability of Spermatic Cord After Torsion" Urology, V(1):133-136, (1975).

Sekijima et al., "An lntraoperative Fluorescent Imaging System in Organ Transplantation," Transplantation Proceedings, 36:2188-2190, (2004).

Sherif et al., "Lymphatic Mapping and Detection of Sentinel Nodes in Patients with Bladder Cancer," The Journal of Urology, 166:812-815, (2001).

Soltesz et al., "Intraoperative Sentinel Lymph Node Mapping of the Lung Using Near-Infrared Fluorescent Quantum Dots," Ann Thorac Surg 79:269-277, (2005).

Still et al., "Diagnosis of burn depth using laser-induced indocyanine green fluorescence: a preliminary clinical trial," Burns, 27:364-371, (2001).

* cited by examiner

METHOD AND APPARATUS FOR VASCULATURE VISUALIZATION WITH APPLICATIONS IN NEUROSURGERY AND NEUROLOGY

RELATED APPLICATIONS

This application claims the benefit of PCT Application Ser. No. PCT/US2006/016101, filed Apr. 26, 2006; which claims the benefit of U.S. provisional Ser. No. 60/674,890, filed Apr. 26, 2005, the disclosures of all of which are incorporated herein by reference in their entirety as if fully set forth herein.

FIELD OF THE INVENTION

The invention relates generally to the field of medical imaging. Certain embodiments of the invention provide methods for imaging vasculature in a subject. Certain other embodiments provide systems which are useful for imaging vasculature in a subject.

BACKGROUND OF THE INVENTION

Imaging of biological tissues and organs assists doctors in both diagnosis and treatment. A variety of medical techniques which are suitable for imaging biological tissues and organs are known. These include traditional x-rays, ultra-sound, as well as magnetic resonance imaging (MRI), and computerized tomography (CT). A variety of dyes used in medical imaging have also been described including radio opaque dyes, fluorescent, as well, as colorimetric dyes (see e.g., U.S. Pat. Nos. 5,699,798; 5,279,298; 6,351,663; and U.S. patent application Ser. No. 10/365,028). Imaging techniques and systems using fluorescent dyes have been described for the heart and eye (see, U.S. Pat. Nos. 5,279,298 and 6,915,154; and U.S. patent application Ser. No. 10/619,548, all of which are incorporated by reference in their entirety). Some dyes can serve both an imaging function, as well as a therapeutic function (see, e.g. U.S. Pat. No. 6,840,933). It would be useful to provide imaging methods and systems that could be used to view vasculature maladies associated with the central nervous system and/or brain.

One example of a malady affecting the brain is cerebral arteriovenous malformation (AVM). AVM is a disorder of the blood vessels in the brain, in which there is an abnormal connection between the arteries and the veins. Thus, a connection between arteries and veins occurs without having the normal capillary bed between them. Arteriovenous malformations vary in their size and location within the brain. It is a congenital disorder. The AVM consists of blood vessels termed "nidus" (nest) through which arteries connect directly to veins, instead of through the elaborate collection of capillaries. Over time, the AVM tends to enlarge as the great pressure of the arterial vessels can not be handled by the veins that drain out of it. This causes a large collection of worm-like vessels to develop (malform) into a mass capable of bleeding at some future time. These malformations are most likely to bleed between the ages of 10-55.

There are often no symptoms until complications occur, which involve rupture of the AVM and a resulting sudden bleed in the brain i.e. a hemorrhagic stroke. When symptoms do occur before an AVM ruptures, they are related to smaller and slower bleeding from the abnormal vessels, which are often fragile because their structure is abnormal.

In more than half of patients with AVM, hemorrhage from the malformation is the first symptom. Depending on the location and the severity of the bleed, the hemorrhage can be profoundly disabling or fatal. The risk of bleeding from an AVM is approximately 2-4% per year. Cerebral arteriovenous malformations occur in approximately 3 out of 10,000 people. If an AVM bleeds once, the risk is greater that it will bleed again in the future. Intracerebral or subarachnoid hemorrhages are the most common first symptoms of cerebral arteriovenous malformation (see, e.g., Ojemann R G, Ogilvy C S, Heros R C, Crowell R M, eds. *Surgical Management of Cerebrovascular Disease*, Third edition, 2005, Williams & Wilkins, Baltimore).

The first symptoms often include headache, seizure, or other sudden neurological problems, such as vision problems, weakness, inability to move a limb or a side of the body, lack of sensation in part of the body, or abnormal sensations.

Open brain surgery, endovascular treatment, and radiosurgery are some of the treatments used. Often these treatment options will be used in combination. Very large AVMs may short-circuit blood flow enough to cause cardiac decompensation in which the heart is unable to pump enough blood to compensate for bleeding in the brain. This condition is usually identified in infants and young children.

Surgery is dependent upon the accessibility and size of the lesion and the status of the patient at the time of surgery. Open brain surgery is the actual removal of the malformation in the brain through an opening made in the skull.

Systems and methods which provide for imaging vasculature associated with AVM would assist the surgeon in locating the AVM and thus would aid in achieving a successful outcome to the procedure. Similarly, the same methods and systems could be used to confirm that the AVM has been removed.

Traditional imaging methods used in the context of AVM, such as measuring arterial pulsation or angiography using digital subtraction are either unreliable or expensive and inconvenient to be used during surgery (see, e.g., Wrobel et al., 1994, *Neurosurgery* 35(5):970; Martin et al., 1990, *J. Neurosurg.* 73:526). A need therefore exists for improved imaging methods and systems which provide for the rapid, accurate and inexpensive imaging of maladies affecting the vasculature associated with the brain and central nervous system, e.g., AVM.

SUMMARY OF THE INVENTION

In certain embodiments, the invention provides a method of intra-operatively confirming the removal of at least one vessel comprising an arteriovenous malformation in a subject. The method includes the steps of (a) administering a fluorescent dye to the recipient subject; (b) applying a sufficient amount of energy to the vessel such that the fluorescent dye fluoresces; (c) obtaining a fluorescent image of the vessel; and (d) observing the image to determine if a fluorescent signal stops at a point of removal of the vessel, wherein a lack of a fluorescent signal downstream of the point of removal indicates the arteriovenous malformation has been removed.

In certain embodiments, the invention provides a method of intra-operatively locating at least one vessel comprising an arteriovenous malformation in a subject. The method includes the steps of (a) administering a fluorescent dye to the recipient subject; (b) applying a sufficient amount of energy to the vessel such that the fluorescent dye fluoresces; (c) obtaining a fluorescent image of the vessel; and (d) observing the image to determine if the fluorescent signal leaks from a vessel suspected of comprising an arteriovenous malformation, wherein a leak of a fluorescent signal from a vessel suspected of comprising an arteriovenous malformation indicates the presence of an arteriovenous malformation.

In some embodiments, the invention provides a portable system useful for imaging at least one vessel comprising an arteriovenous malformation comprising a fluorescent dye in a subject comprising (a) an energy source capable of emitting sufficient energy such that the fluorescent dye fluoresces; and (b) an imaging head.

An imaging method is further provided in certain embodiments that includes the steps of: (a) administering a fluorescent dye to the recipient subject; (b) applying a sufficient amount of energy to the vessel such that the fluorescent dye fluoresces; (c) obtaining a fluorescent image of the vessel; and (d) determining the presence or absence of an occlusion or stenosis, wherein jagged edges, or a change in thickness indicates a stenosis and a discontinuous signal indicates an occlusion.

BRIEF DESCRIPTION OF THE DRAWINGS

The above and further advantages of the invention may be better understood by referring to the following description in conjunction with the accompanying drawings in which:

FIG. 1 shows an example of an electrical configuration.

DETAILED DESCRIPTION

Figure 1:
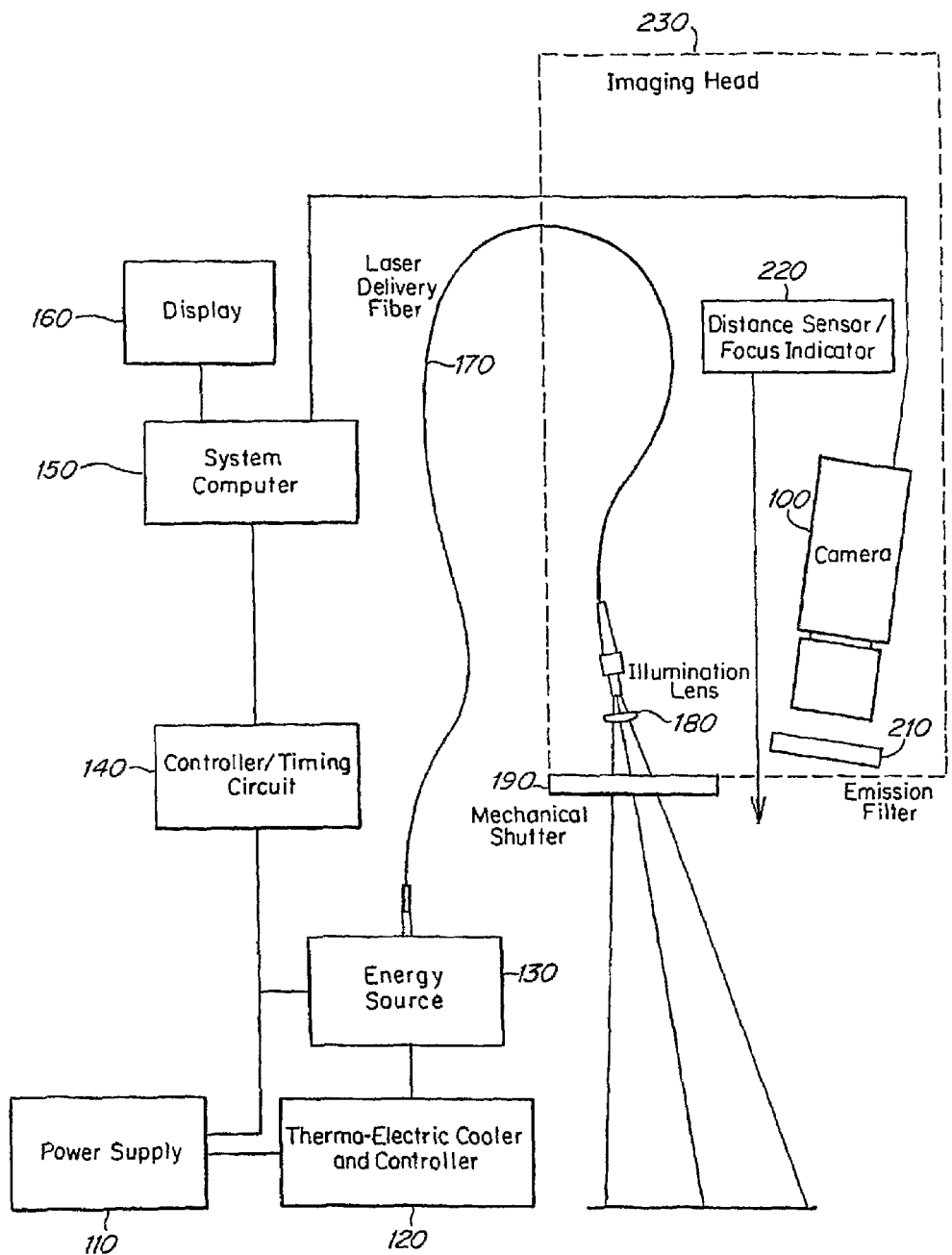
FIG. 1 is a schematic diagram showing one embodiment of the system of the invention.

Hereinafter, aspects in accordance with various embodiments of the invention will be described. As used herein, any term in the singular may be interpreted to be in the plural, and alternatively, any term in the plural may be interpreted to be in the singular.

Definitions

"Approximately", "substantially" and "about" each mean within 10%, preferably within 6%, more preferably within 4% even more preferably within 2%, and most preferably within 0.5%.

"Computer" as used herein, refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer system. A bus controller is provided for controlling the bus. An interrupt controller is used for receiving and processing various interrupt signals from the system components. Mass storage may be provided by diskette, CD ROM or hard drive. Data and software may be exchanged with computer system via removable media such as the diskette or CD ROM. A CD ROM drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the system to be interconnected to a local area network (LAN) or a wide area network (WAN). Operation of the computer is generally controlled and coordinated by operating system software, such as the Solaris operating system, commercially available from Sun Microsystems, the UNIX® operating system, commercially available from The Open Group, Cambridge, Mass., the OS/2® operating system, commercially available from International Business Machines Corporation, Boca Raton, Fla., or the Windows NT operating system, commercially available from MicroSoft Corp., Redmond, Wash. The operating system controls allocation of system resources and performs tasks such as processing scheduling, memory management, networking, and I/O services, among things. In particular, an operating system resident in system memory and running on the CPU coordinates the operation of the other elements of computer.

As used herein, "wavelength of interest" refers to light in both the visible and infra red spectrum. In another embodiment, it refers to light in only the infra red spectrum. In yet another embodiment, it includes light at the wavelength at which ICG fluoresces. In yet another embodiment, it includes light between about 825 and about 835 nm. In yet another embodiment, it includes light wavelength(s) at which one or more other fluorescent dyes emit energy when excited. The invention provides systems and methods for imaging neurovasculature, e.g., the vasculature associated with AVM or an aneurysm. The neurovasculature of interest may be associated with the central nervous system (e.g., brain, or spine) or the peripheral nervous system (e.g., in a limb). Surgical removal of AVMs is not without serious risk. In certain embodiments the instant invention seeks to minimize the risks associated with surgery to remove AVMs by providing imaging systems and methods which permit the surgeon to intra-operatively locate the position of the AVM, and thus prevent damaging or cutting vasculature not associated with AVM and hence decrease the chance of stroke and other iatrogenesis. In other embodiments the systems and methods of the invention may also be used to confirm that the AVM has been successfully removed.

Methods of the Invention

In certain embodiments the invention provides a method for imaging at least one vessel, in a subject, wherein the vessel is associated with an AVM. The vessel may include an artery or a vein or a nidus associated with an AVM. Associated refers to vessels which either feed or drain the AVM or are vessels which comprise the AVM. The image may be obtained intra-operatively. Thus the vessel may be surgically exposed.

The method comprises administering a fluorescent dye to the subject. Exposing the vessel to a form of radiant energy such that the fluorescent dye fluoresces and obtaining an image of at least one vessel associated with the AVM. By observing the fluorescent image the surgeon can locate the AVM in the subject. Blood flow through the AVM may appear different. As an example, but not as a limitation, the vessel may appear to have small leaks in it due to the weakened structure of the vessels comprising the AVM. In this case the fluorescent dye would leak into the extra-vascular tissue. In addition, once the AVM has been removed the surgeon can confirm that there are no remaining leaky vessels and that the surgically cut vessels have been sealed properly.

The invention also contemplates obtaining a plurality of images. The plurality of images may be compared to each other to determine the effectiveness of a therapy, e.g. an administered pharmaceutical compound, a surgical procedure.

In yet another embodiment, the invention provides a method for imaging to determine the absence, presence or perfusion of tumors. The method includes the steps of (a) selecting a portion of body tissue to be imaged, (b) obtaining at least one angiographic image of that body tissue, (c) and examining the at least one angiographic image to assess the extent of blood flow within the selected body tissue. Since tumors are often inappropriately perfused, the physician may be able to determine not only the presence or absence of a tumor, but also its size and margins. The information can be used to not only locate tumors but to also later confirm that a procedure to remove the tumor has been successful. In such embodiments, the tissue of interest will be imaged before the tumor-removal procedure to locate or confirm the position of a tumor and also after the procedure to confirm the tumor has been successfully removed.

In certain embodiments the invention provides a method of determining the patency of a vessel comprising a lumen. In some embodiments patency may be determined by visually inspecting an image of the vessel. As an example, but not as a limitation, a continuous signal from a dye that is uniform in thickness may indicate patency. As another non-limiting example an image displaying jagged edges, or a change in thickness may indicate stenosis. Similarly a discontinuous signal may indicate occlusion.

Subject as used herein, refers to any animal. The animal may be a mammal. Examples of suitable mammals include, but are not limited to, humans, non-human primates, dogs, cats, sheep, cows, pigs, horses, mice, rats, rabbits, and guinea pigs.

Dyes

Suitable fluorescent dyes include any non-toxic dye which fluoresces when exposed to radiant energy, e.g. light. In certain embodiments the dye is a fluorescent dye that emits light in the infra red spectrum. In certain embodiments the dye is a tricarbocyanine dye such as indocyanine green (ICG). In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The aforementioned dyes may be mixed or combined in certain embodiments. In some embodiments dye analogs may be used. A dye analog includes a dye that has been chemically modified, but still retains its ability to fluoresce when exposed to radiant energy of an appropriate wavelength.

In some embodiments the dye may be administered intravenously, e.g., as a bolus injection. In some embodiments the bolus injection may comprise a volume of about 0.5 ml. In other embodiments the bolus injection may comprise a volume in the range of about 0.1 ml to about 10 ml. In some embodiments the dye may be administered parenterally. Where multiple dyes are used they may be administered simultaneously, e.g. in a single bolus, or sequentially, e.g. in separate boluses. In some embodiments the dye may be administered by a catheter or cannula, e.g. during a minimally invasive procedure.

The dye may be administered at a suitable concentration such that the fluorescence may be detected when the appropriate wavelength of radiant energy is applied. In some embodiments where the dye is ICG a suitable concentration is about 0.03 mg/ml at the site of detection. In other embodiments a suitable concentration of ICG is in the range of about 0.003 mg/ml to about 75 mg/ml. In some embodiments the ICG is administered in the range of about 1 mg/kg body weight to about 6 mg/kg body weight. In yet other embodiments the dye is administered at a concentration of about 0.5 mg/kg body weight. In still other embodiments the dye is administered in a range of about 0.01 mg/kg body weight to about 3 mg/kg body weight. In certain embodiments a suitable maximum daily dose of ICG may be administered to a subject. The maximum daily dose may be in the range of about 70 mg-about 140 mg.

The dye may be provided as a lyophilized powder or solid. In certain embodiments it may be provided in a vial, e.g. a sterile vial which may permit reconstitution with a sterile syringe. It may be reconstituted using any appropriate carrier or diluent. Examples of carriers and diluents are provided below. In certain embodiments the dye may be reconstituted at a concentration in the range of about 0.001 mg/ml-100 mg/ml. In other embodiments the dye is reconstituted to a concentration of about 10 mg/ml, about 20 mg/ml, about 30 mg/ml, about 40 mg/ml, about 50 mg/ml. The dye may be reconstituted, e.g., with water, immediately before administration.

In certain embodiments the dye may be administered to the subject less than an hour in advance of obtaining an image. In some embodiments the dye may be administered to the subject less than 30 minutes in advance of obtaining an image. In yet other embodiments the dye may be administered at least 30 seconds in advance of obtaining an image. In still other embodiments the dye is administered contemporaneously with obtaining an image.

Diluents and Carriers

Any diluent or carrier which will maintain the dye in solution may be used. As an example, in certain embodiments where the dye is ICG the dye may be reconstituted with water. In other embodiments where the dye is ICG, the dye may be reconstituted with an alcohol, e.g. ethyl alcohol. In some embodiments once the dye is reconstituted it may be mixed with additional diluents and carriers. In some embodiments the dye may be conjugated to another molecule, e.g., a protein, a peptide, an amino acid, a synthetic polymer, or a sugar, e.g., to enhance solubility or to enhance stability.

Additional examples of diluents and carriers which may be used in the invention include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polyoxylethylated fatty acids, and mixtures thereof. Additional buffering agents may optionally be added including Tris, HCl, NaOH, phosphate buffer, HEPES.

Radiant Energy

In certain embodiments of the invention radiant energy is applied to the vessels in the region suspected of having an AVM or other neurovasculature of interest in an amount sufficient to cause a fluorescent dye to fluoresce thereby permitting at least one vessel associated with the AVM to be imaged. In some embodiments the energy is light energy. In some embodiments the source of the light energy is a laser. An example of a suitable laser is the Magnum 3000 (Lasiris St-Laurent, Quebec, Canada), however, the skilled artisan will appreciate many other suitable lasers are commercially available. The laser may be comprised of a driver and diode. Preferably, the laser is a high power laser diodes (HPLDs). Examples of HPLDs include AlInGaAsP lasers and GaAs lasers which are well known in the art. Such sources can be single diodes (single emitters), or diode-laser bars, which are made from edge emitting semiconductor chips. The laser may optionally include a filter, e.g. a bandpass filter, to ensure that the emitted radiation is of a substantially uniform wavelength. The laser may comprise optics for diverging the laser. The optics may be adjustable permitting variation in the field of illumination. The adjustable optics may also be used to provide even illumination over a given area.

In some embodiments the laser output is continuous or quasi continuous. In other embodiments the laser output is pulsed. The pulsed output may be synchronized with image acquisition by using a pulse generator. In some embodiments the laser pulse may last for at least 3 femtoseconds. In some embodiments the laser output lasts for about 30 seconds. In other embodiments the laser output lasts about 0.5 seconds-about 60 seconds. A suitable repetition rate for the pulsed laser may be in the range of e.g., 1 Hz-80 MHz, 10 Hz-100 Hz, 100 Hz-1 kHz, 1 kHz-100 kHz, 100 kHz-80 MHz. In some embodiments the laser may be operated at power output of 2.2 watts. In other embodiments the laser may be operated at power output in the range of 1-4 watts. In still other embodiments the average power is less than 5 watts.

In some embodiments the source of the light energy is an incandescent light with an appropriate filter so as to provide a suitable wavelength of light to induce the fluorescent dye to fluoresce. In yet other embodiments the light source is light emitting diode (LED). In some embodiments the light energy may have a wavelength in the range of 150 nm-1500 nm. In other embodiments the light energy may be comprised of infra red light. In some embodiments the administered light has a wavelength of about 805 nm. In other embodiments the administered light has a wavelength in the range of about 805 nm-850 nm. The light energy may be administered at a wavelength which is shorter than the collection wavelength, i.e. detection wavelength. The light energy may be administered diffusely so as not to damage the irradiated tissue. In some embodiments the light is administered over an area of about 1 inch×1 inch. In another embodiment, the field of view is between about 0.5 inches to about 2 inches in one dimension, and between about 0.5 inches to about 2 inches in a second dimension. In yet another embodiment, the first and second dimensions are both between about 0.5 inches and about 1.5 inches. In some embodiments, the field of view ranges from about 1 cm to about 20 cm in each dimension. Preferably, the field of illumination is about equal to the field of view. The irradiance is in the range of about 15-25 $mW/cm^2$, and in some embodiments between about 18-22 $mW/cm^2$. Appropriate fields of view and illumination and irradiance levels can be achieved by modifying projection optics that are in optical communication with a laser light guide, as is well known to the skilled artisan. As described above, multiple dyes may be used in some embodiments. In these embodiments, multiple light sources may be used, e.g., a first laser to excite a first dye and a second laser to excite the second dye. The skilled artisan will understand that the light source will be chosen or configured to excite a particular dye. In another embodiment, a single light source may be configured to excite multiple dyes, e.g., by alternating the wavelength at which energy is emitted.

Image Acquisition

Image acquisition may be achieved using any sensor capable of detecting a fluorescent signal. Examples include silicon based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan).

In certain embodiments an endoscope may be used, e.g., for an interventional application. It may include a sensor. The endoscope may additionally comprise a source of radiant energy. The endoscope may be comprised of optical fibers. In certain other embodiments a microscope comprising a sensor may be used, e.g., a surgical microscope. In another embodiment the sensor comprises a video camera.

In certain embodiments the sensor may capture images at the rate of at least 10 per second, at least 15 per second, at least 20 per second, at least 30 per second, or at least 50 per second. Thus in certain embodiments the invention contemplates a plurality of images. In other embodiments the invention contemplates one image.

The camera may be comprised of a means for focusing the image. In certain embodiments the invention contemplates a manual means for focusing an image. In other embodiments the invention contemplates an automated means for focusing an image. The camera may further be comprised of a lens system that permits magnification of an image field.

In one embodiment the relative positioning of the camera and laser is fixed so as to enhance clarity and minimize background noise. In this embodiment the laser is located at an angle of less than about 85° with respect to the axes of the laser and the camera. In another embodiment the laser is located at an angle from about 20° to about 70° with respect to the axes of the laser and the camera.

In certain embodiments the camera relays the captured image to an analog to digital converter and then through image capture and processing software running on a computer. The digital image of the fluorescing agent, corresponding to the AVM or other neurovasculature of interest may then be displayed on a monitor and recorded by the computer or a peripheral device. The image may be stored in any suitable medium, e.g., a hard drive, an optical disk, magnetic tape. The camera may also direct images to a television/VCR system such that the images may be displayed in real time, recorded and played back at a later time.

Systems of the Invention

The invention provides a system for imaging at least one vessel associated with an AVM or other neurovasculature of interest, see, e.g., FIG. 1. The system may be used intraoperatively during surgery on an AVM to visualize at least one surgically exposed vessel associated with the AVM.

System Overview

FIG. 1 illustrates an example of an electrical configuration of a system of the invention. In one embodiment, power supply 110 provides energy to thermoelectric cooler and controller 120, energy source 130 and controller/timing circuit 140. The controller 120 controls the temperature of energy source 130. For example, the temperature of a diode laser affects its operating wavelength, (e.g., a 0.3 nm shift per degree Celsius). In some embodiments, as described below, the energy source 130 may not be a diode laser, and hence a controller 120 may not be necessary. Controller/timing circuit 140 times the energy source 130 to the detector/camera 100 through computer 150. System computer 150 receives instructions from computer 150. It also includes image processing software on computer 150 readable medium. Computer 150 is in electrical communication with camera 100 and display 160. Display 160 receives image data from computer 150 and displays it. As described above, in some embodiments, the energy source 130 is a laser. It has a fiber 170 through which light energy is transmitted. Fiber 170 connects to illumination lens 180 through which light is illuminated when mechanical shutter 190 is open. An emission filter 210 may be used to filter light above or below the wavelengths at which the fluorescent dye is excited. In other embodiments, the energy source 130 may be an LED. It would directly illuminate the tissue of interest (i.e., no fiber 170 may be required.) The light energy irradiates a tissue of interest. Camera 100 captures radiation emitted by the dye after it is excited and transmits detected data to computer 150. The lens 180, fiber 170, and camera 100 are part of imaging head 230. The head 230 may be an articulating head. In some embodiments, head 230 further includes a distance sensor/focus indicator 220. The components of the systems of the invention are further described herein.

In certain embodiments, the system comprises: a) an energy source 130 capable of emitting sufficient energy such that the fluorescent dye fluoresces; and b) an imaging head 230. The system is configured for use with the methods disclosed herein. In some embodiments, the system further includes c) an articulating arm; d) a computer 150 and monitor; e) image processing software; f) an electrical power source; and g) a housing for containing a-f, wherein the housing is portable and comprises at least 2 wheels. The wheels may have locks to prevent unwanted movement. In some embodiments the system may also comprise at least one of the following: a motion sensor; a distance sensor 220; a sterile drape; and a printer. The system may further comprise an instruction booklet. The system may be portable and thus may be transported in and out of the operating room. The system may be self standing and thus does not require to be hand held by a physician, nurse or a technician. In some embodiments, the system further comprises a fluorescent dye.

The imaging head 230 may be comprised of a sensor, e.g., a camera 100. The imaging head 230 may, in some embodiment, also contain the energy source 130, e.g. the laser. In some embodiments the laser contained within the imaging head 230 provides a nominal ocular hazard distance (NOHD) of about 27 cm. The NOHD is the distance at which the beam irradiance or radiant exposure equals the corneal maximum permissible exposure. In certain embodiments the imaging head 230 is joined to the housing by virtue of the articulating arm.

The articulated arm provides six degrees of freedom for the imaging head 230. The imaging head 230 can be translated and positioned in three linear movements (X, Y and Z), and three angular movements (pitch, yaw and roll). Pitch is the rotation of the imaging head 230 about the Y axis. Roll is the rotation of the imaging head 230 about the X axis and Yaw is the rotation of the imaging head 230 about the Z axis.

The articulated arm is comprised of three sections, the horizontal section, the articulated section and the yoke. The horizontal section attaches to the cart, or housing, and provides movement along the horizontal axis (X axis and also roll) and can move in 270 degrees of freedom. The articulated section is hinged in the middle of its length forming two segments. Each segment can rotate with 90 degrees of freedom in one axis. The articulated section provides movement in the vertical axis (Z and also X and Y). The yoke section is a curved section that attaches to the distal end of the articulated section. The yoke has two rotational attachment points. One point attaches to the articulated arm and the other to the imaging head 230. The yoke provides the imaging head 230 two rotational degrees of freedom (pitch and roll). The articulating arm thus provides a means for positioning the imaging head 230 directly over the subject.

In certain embodiments the imaging head 230 is positioned above the patient and the appropriate field of view is obtained with the aid of real time images on a computer monitor. The physician may adjust the range of focus, e.g., by intermittently observing images on the computer monitor. In another embodiment two or more laser pointers (e.g., light sources) are provided, e.g., one at each end of the imaging head 230. These laser pointers may be the same energy source 130 as is used for exciting the fluorescent dye, or may be a different energy source 130. The laser beams may radiate green light or light at other or multiple wavelengths in the visible spectrum. The laser pointers are configured to emit irradiation in non-parallel beams. They emanate towards the patient or area of interest that is to be imaged. They may, for example, emanate from the imaging head.

The two laser pointers are separated by a fixed distance and angled such that they are in the form of two sides of a triangle. The result is that the two points of light will be coincident and form a single point of light at a particular distance from the laser pointers (e.g., the approximate distance which the imaging head must be from the area of interest in order to obtain a sufficiently clear image). The detectors detect infrared radiation in the area that is to be imaged in other embodiments of the invention (e.g., they detect in the approximate area of a human tissue, organ, vessel of a subject). Data obtained by the detectors is transmitted to computer 150 having image processing software. The software detects infrared radiation and thus pixels indicative of the infrared beams have a different intensity than other pixels. The image processing software can thus determine if there are zero, one, or two distinct dots (indicative of infrared radiation) in a row or column (or multiple rows or columns) in the imaged area. "Distinct" means that the set is surrounded by pixels that are not indicative of infrared radiation. When the imaging head is moved to a shorter distance or longer distance from the imaged area, the two points of light will no longer be coincident in the imaged row(s) or column(s). When the platform is moved away from the target distance the same effect happens. The skilled artisan will understand that the beams must be relatively narrow (i.e., one beam cannot include the entire field of view).

In one embodiment, the laser pointers are configured so that the two beams converge at the approximate focal point of the light source used to excite the fluorescent dye. The laser beams from the pointers point down toward the patient and provide a means of focusing the camera 100, without the need to look away from the patient, e.g., at a computer screen. When the two dots from the laser beams converge the centre of the image is determined. The laser beams from the pointers point down toward the patient and provide a means of focusing the camera 100, without the need to look away from the patient, e.g., at a computer screen. If the doctor, nurse or technician determines that the beams do not converge in the approximate area where the patient is to be imaged, he can move the imaging head 230 or optics (e.g., detector(s)) with his hand until the laser pointers converge in the actual or approximate area where the subject will be imaged. The device may be provided with buttons that allow for manually turning the laser pointers on and off. The buttons may be covered by the sterile drape, but may protrude enough to facilitate ease in switching the laser pointers on and off.

In certain embodiments, I the imaging head 230 may include two lasers or laser pointers that emit radiation in the infrared spectrum. This laser source may emit radiation such as at 900 nm, 950 nm or some other wavelength or combination of wavelengths. The infrared radiation is detected by detectors described herein and detected to computer 150 including image processing software. Images of the laser beam may be displayed visually on a display. Thus, a doctor or other attending professional can determine that the energy source 130 is positioned to provide a focused image of excited fluorescent dye without exciting the fluorescent dye (i.e. before the start of the imaging procedure).

In yet another embodiment, the infrared beams are detected by detectors and information about them is relayed to the image processing software. The image processing software determines whether there are zero, one or two distinct dots or sets of pixels indicative of infrared light in the imaged area. If a determination is made that the imaging head is at an incorrect height because there is more or less than one distinct set of pixels indicative of infrared light as imaged by the detectors, the height of the imaging head or detectors may be adjusted through mechanical means, such as instructions from computer 150 to a motor to turn a lead screw mechanism to obtain a linear displacement, and thus adjust the height of the imaging head or the optics (e.g., detectors), by human intervention, or by other means. The determination of whether the beams converge in the area to be imaged may be made once or more than once during a procedure. For example, it may be determined once every 10, 20, 30, 40, 50, 60 or some other number of frames. In embodiments where the height of the detectors or imaging head is moved without human intervention, the computer 150 may first instruct the head or optics be moved in one direction. The detectors then reimage the area of interest and the data is then sent to computer 150. If the image processing software determines that there are two distinct sets of pixels indicative of infrared radiation that are further apart than in the previous image, the computer 150 instructs the motor to move the lead screw mechanism in the opposite direction. Multiple images may be obtained at different heights of the imaging head and/or detectors until there is one distinct set of pixels indicative of infrared radiation in the detected area.

Figure 3:
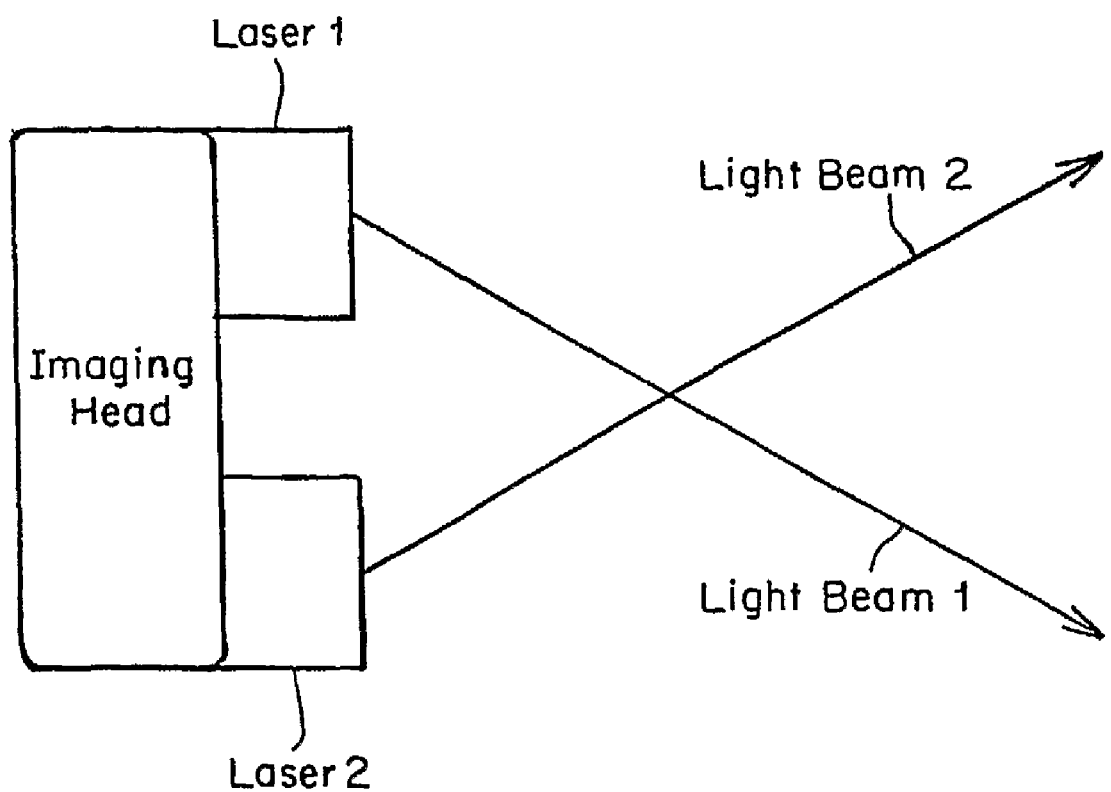
FIG. 3 illustrates an embodiment of the invention

FIG. 3 illustrates two light sources (e.g., laser pointers) that each emit a beam, both beams converging at the focal distance.

In certain embodiments the computer is a personal computer 150 comprising at least 512 Megabytes of random access memory (RAM) and at least 10 Gigabytes of storage. In some embodiments the computer may contain a Pentium IV processor (Intel, Santa Clara, Calif.). In some embodiments the computer 150 may also have a CD and DVD drive. The drive may have read and write functionality. The system also provides image processing software. The computer 150 is in electrical communication with the energy source 130 and detectors as described herein.

Figure 2:
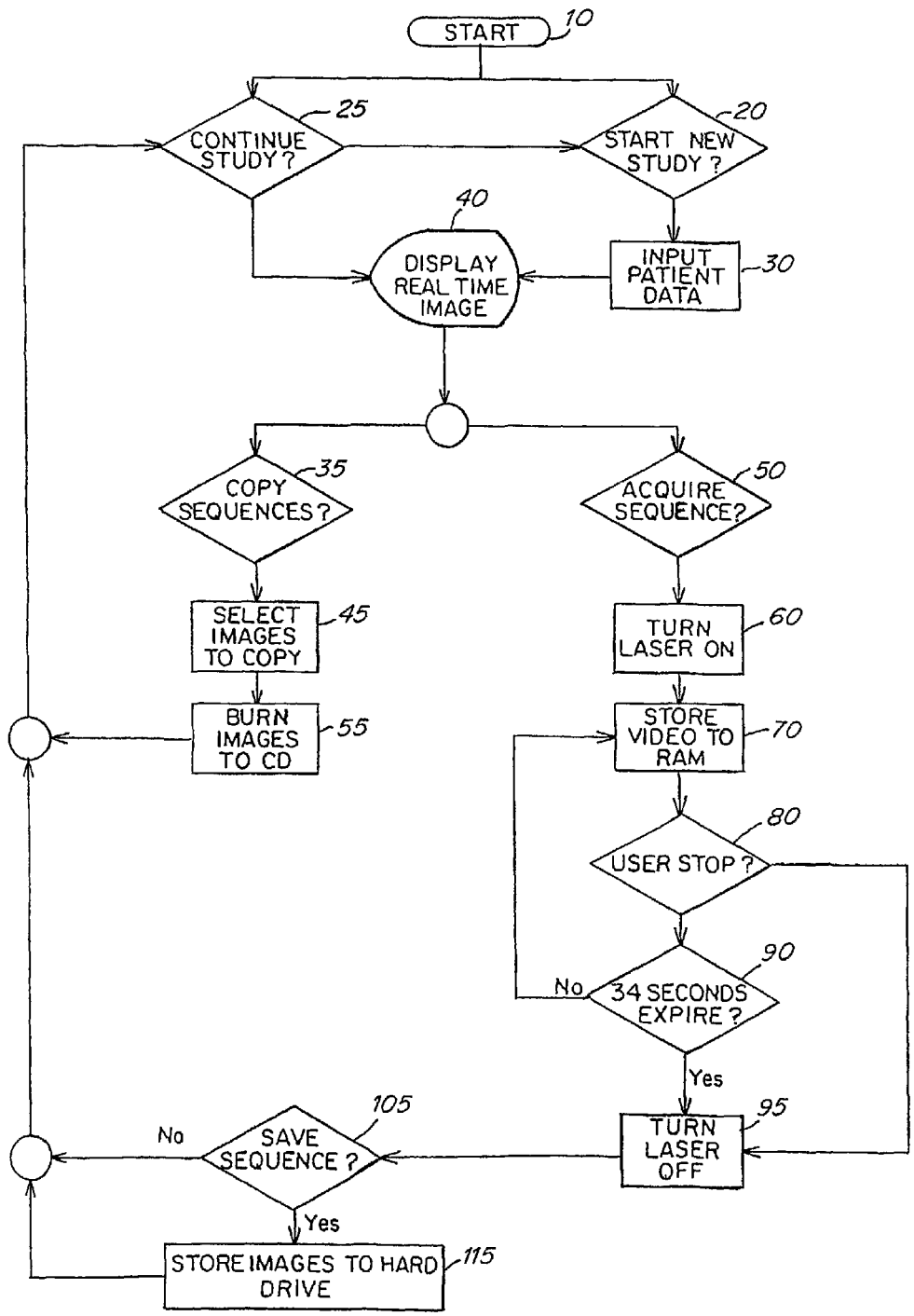
FIG. 2 illustrates imaging software that may be used in certain embodiments of the invention.

FIG. 2 illustrates a flowchart of software that may be used within the scope of the present invention. The skilled artisan will understand that such software includes instructions stored on computer-readable medium. When executed, the software program provides instructions to the computer processor as described below. The skilled artisan will further understand that the computer is in communication with the laser, sensor and display as described herein.

At start (step 10) the user may be presented with multiple dialog boxes or other common user interface paradigms. For example, the user may be queried about whether he wishes to start a new study (step 20). If the user indicates that he does, he may be instructed to input or otherwise selects a patient for the study. For example, the user may be prompted to choose a name from a list linked to a database that is accessible to the computer. Alternately, he may be prompted to input a patient identifier. The computer may then access the database to determine the existence of additional information associated with the patient, and preferably to obtain such information. In a preferred embodiment, the software requires the user to input or otherwise select values for Patient First Name, Last Name and ID number fields. Most preferably, sufficient information is inputted or otherwise loaded so that images may be stored according to the Digital Imaging and Communications in Medicine (DICOM) standard. The DICOM Standard is a product of the DICOM Standards Committee and its many international working groups. Day-to-day operations are managed by the National Electrical Manufacturers Association (Rosslyn, Va.). The standard is publicly available at the website http://medical.nema.org/, and is incorporated herein by reference in its entirety.

After patient data is inputted, the monitor or other display displays images captured by the camera or other sensor in communication with the computer (step 40). At this point, the user can change the position, orientation, gain or other parameter of the camera to obtain a desired view of the patient.

Alternately, the user may choose to continue a study (step 25) at start 10. Upon such indication, the process proceeds to step 40.

Once the image is displayed, the user is prompted to indicate whether he wishes to copy sequences (step 35) or acquire sequence (step 50). The term "sequences" refers to data associated with real-time images captured by a camera or other sensor in communication with the computer. Once the user indicates that he wants to acquire images from the sensor in step 50, the computer causes the laser to turn on, and it stores the video sequence obtained from the sensor in RAM (step 70). Real time images continue to be displayed on the display. The user is then queried about whether he wishes to turn the laser off (step 80). If he indicates that he does, the computer causes the laser to shut off (step 100). Alternately, if the user does not indicate that he wants to shut off the laser, the computer determines whether a pre-determined amount of time (e.g., 34 seconds) has elapsed from step 60. Once that pre-determined amount of time has elapsed, the computer causes the laser to shut off. The video sequences continue to be stored in RAM until the laser is turned off. Once the laser is turned off, the user is queried as to whether he wishes to save the sequence (step 110). If he indicates in the affirmative, then the sequences are stored to hard drive (step 120) or other media.

Returning now to step 40 for purposes of describing the software, once the real time image is displayed, the user is queried as to whether he wishes to copy sequences (step 35). If the user indicates that he does, the images associated with the study are selected and burned on compact disk or other selected media (step 55). Alternately, the software may allow the user to select specific images for storage on selected media. Preferably, the image(s) are stored in a format that is compatible with a picture archiving and computer system, for example in a DICOM format.

In another embodiment, the camera may also direct images to a television/VCR system such that the image(s) may be displayed in real time and/or recorded and played back at a later time. Since the image(s) may be used to guide all or part of the surgical procedure, the image(s) may be displayed through out the length of the surgical procedure. In other embodiments, the image(s) may be displayed for less than the entire length of the surgical procedure. In another embodiment the software permits manipulating the images after acquisition, such as zooming, region of interest selection, change of brightness and contrast, and displaying multiple images simultaneously.

In certain embodiments the image processing software permits selection of the optimal image for analysis. In some embodiments the image processing software may permit manipulation of contrast. In some embodiments the image processing software can permit manipulation of resolution. In another embodiment the image processing software can permit manipulation of the number of pixels in a field. In another embodiment the image processing software may permit control of the rate at which images are acquired. The software may be able to determine the relative contrast of one image with another, and thus select the images having the greatest contrast for analysis, e.g., images of AVMs emitting detectable fluorescence.

In certain embodiments the software may be used to compare images of pre and post treatment vessels to determine flow within the vessel, e.g., blood flow. The comparison may be performed by calculating and comparing the area of fluorescence (e.g., the number of pixels associated with the fluorescing dye) in pre and post treatment images corresponding to a selected area of interest in the vessel. In other embodiments the relative maximum fluorescent intensity may be calculated, e.g. pre and post-treatment. A greater number of pixels or a greater fluorescent intensity in a post treatment vessel, as compared to a pre-treatment vessel, may be indicative of patency. Conversely, fewer (or no pixels) or less fluorescent intensity may be indicative of stenosis or occlusion.

The system also provides, in certain embodiments, for a housing to contain the computer, the monitor, the electrical supply, the printer, and the imaging head. The housing may be portable to permit movement within the operating room or alternatively to permit movement of the system in and out of the operating room. In some embodiments the housing is comprised of at least two wheels. In other embodiments the housing is comprised of four wheels. The wheels may have locks to prevent unwanted movement.

In certain embodiments the housing has a width of about 30 inches, a depth of about 35 inches and height of about 82 inches. In certain embodiments the housing width is less than 40 inches. In certain embodiments the housing width is less than 45 inches. In certain embodiments the depth is less than 45 inches. In certain embodiments the height is less than 102 inches. The housing is not hand held, and thus the system is not required to be hand held.

The electrical power supply may be comprised of a lock in some embodiments. The lock serves as a safety device to prevent inadvertent activation of the system, particularly activation of the laser.

In some embodiments the system may be comprised of a motion detector. The motion detector determines if the imaging head moves. In certain embodiments the system comprises a distance sensor. The distance sensor determines the distance between the imaging head and another object, e.g. the subject. In some embodiments it incorporates a visual display which provides feedback to a physician so that the laser and camera may be located at a distance from the tissue of interest that is optimal for capturing high quality images, thereby minimizing the need for focusing the camera during the procedure.

The motion sensor and distance sensor may each be located on the imaging head, for example.

In some embodiments the system comprises a sterile drape. The sterile drape covers the articulating arm to prevent or minimize the risk of contamination of the subject. The sterile drape may have an aperture in it. The aperture may be covered with a material which is capable of transmitting radiant energy, e.g., infra red light generated by a laser.

Apparatus

Certain embodiments of the invention provide an apparatus which may be used for intra-operative imaging e.g., in a surgical suite. The apparatus may be portable so that it may be conveniently transported into and out of an operating room. The apparatus may be free standing and thus not require a physician, nurse or technician to hold it. The apparatus may include one or more systems of the invention. In some embodiments the apparatus may also comprise at least one of the following: a motion sensor; a distance sensor; a sterile drape; and a printer. In some embodiments the housing is comprised of at least two wheels. The wheels may have locks to prevent unwanted movement. In other embodiments the housing is comprised of four wheels. The apparatus may also comprise a focusing device, e.g., at least one focusing laser, e.g. a first and a second laser pointer, the first laser pointer positioned at a first end of the imaging head, and a second laser pointer positioned at a second end of the imaging head. The two laser pointers may be provide radiant light in the green wavelength range and may provide a means of focusing the camera.

The apparatus may be of a suitable size so that it is free standing, but is small enough so as not to provide a significant obstruction in an operating room. In certain embodiments the apparatus has a width of about 30 inches, a depth of about 35 inches and height of about 82 inches. In certain embodiments the apparatus width is less than 45 inches. In certain embodiments the apparatus depth is less than 45 inches. In certain embodiments the apparatus height is less than 102 inches.

In yet other embodiments, the tissue of interest may be imaged with an infrared microscope.

Example 1

This example illustrates a system of the invention. The imaging devices is made primarily of two subsystems that are primarily optical in nature, an illumination subsystem and a detection subsystem. Other subsystems are primarily electrical or mechanical in nature. The illumination subsystem includes a fiber-coupled, infrared laser, a light guide, and a projector lens. The detection subsystem includes a high-quality imaging lens, a narrow band-pass filter, and a CCD camera. The remainder of the system includes a laser, video display, computer and other auxiliary control circuits. The system is designed with an articulated arm with an imaging head. The imaging head contains the imaging and illumination optics and electronics. The articulated arm allows the illumination and imaging systems to be positioned over the field of operation.

Mounted inside this imaging head are the filter and CCD camera, a distance sensor and the light guide and projection lens. A power delivery optical fiber is routed through the articulated arm connecting the laser to the light guide in a low-loss manner.

Illumination Subsystem

A fiber-coupled diode laser with a nominal 2 W output is used as a light source. Wavelength is specified to be 806 nm, which can be reached through use of a thermo-electric cooler attached to the laser mechanical package. For the nominally 30% efficient laser, a heat load of about 7 W would be offered to the surrounding mechanical structure. The temperature of a diode laser affects its operating wavelength, typically 0.3 nm shift per degree C. Additionally, diode lasers have a maximum operating temperature that must never be exceeded. These factors make a temperature control circuit not merely good engineering practice, but also an environmental requirement to achieve long lifetimes (10,000+ hours).

Since modern diode laser manufacturing practice cannot tightly control the power vs. current characteristic, each diode is different, and the maximum power for each unit will be different. The assembly and calibration procedure will individually set the operating current for each unit differently. Since a requirement of the system is to deliver a fixed amount of power to the patient (2.0 W nominal), the illumination subsystem will be designed with a high enough efficiency to guarantee an excess of power delivered when the laser is run at maximum current. During final calibration of the system, the laser diode current will be decreased from maximum to reach the 2.0 W requirements.

The output spectrum of most diode lasers is not "line-like" as in an ideal laser. The spectrum extends over several nm and usually shows prominent peaks. There is also a broad (several 10's of nm wide) low-level pedestal of power. For most fluorescence excitation applications, the broad spectral output of these high-power laser diodes requires an external excitation filter to prevent overlapping of the laser light with the emission band. Prototype experiments performed have shown that this extra filter is not required to achieve a good signal-to-noise ratio in the detected fluorescent image.

Power Delivery Fiber

The system uses a fiber optic cable to carry to the optical power from the laser diode to the optics. The laser's fiber is a multimode fiber, whose core can support many modes of laser transmission. This transfers power without burning the fiber. The core diameter (which sets the effective emitting area) is about 200 microns. The spatial pattern of light emitting from the fiber end is approximately a top hat (with rounded corners) in angle. The output is characterized by the fiber Numerical Aperture (NA) which is the sine of the half angle corresponding to the HWHM. A typical power delivery fiber would have an output NA=0.15, corresponding to a FWHM of about 17°.

Light Guide

To project a square illumination pattern of roughly 76×76 mm the light from the fiber is coupled to a light guide with a square cross section. The light guide may be made of any number of acceptable glasses (e.g. BK7). Note that some optical glasses (e.g. Pyrex) or clear plastics (e.g. polycarbonate) have a large bubble density or high refractive index in-homogeneity. This can lead to significant extraneous losses. The approximate dimensions are 0.25×0.25×4.00 inches. All faces should be polished to approximately 50/80 scratch/dig and flat to within about 5 waves. Protective chamfers (usually a good idea) are to be avoided here since they also can lead to significant extraneous losses.

The purpose of the light guide is to homogenize the laser light. The coupling from the fiber is simply an air gap of a few millimeters. The only requirement is that the end-face of the light guide capture all of the emitted cone of light from the fiber. Thus, for 0.22 NA fiber, the fiber is positioned no further away than 14 mm.

The operation of the light guide is now described. At each point on the exit face, the total laser field is the sum of several fields, some of which have undergone one or more total internal reflections. If scattering losses are kept low, the total power reaching the exit face equals the input power from the fiber, minus Fresnel losses at the end-faces. The radiant distribution is no longer a cone emitted from a small fiber core, but a homogenized, square emitter, with maximum angle equal to the fiber cone angle. Homogeneity improves with length of the light guide. Non-sequential ray-tracing calculations show uniformity with about 20% falloff at the edges after only 4 inches of guide. This is not a diffuse emitter, since for each point on the end-face there are certain definite angles of emission.

Mechanical Interface

The light guide has only a mechanical interface. Preferably, the light guide entry face needs to be within 14 mm of the power delivery fiber exit ferrule. If the cone of light is tight enough, the groove can have a depth of 1 mm without significantly attenuating the light.

The entry face is furthermore tilted with respect to the long axis of the light guide. This allows mechanical access to the Fresnel-reflected beam. A photodiode is placed within this "stray" beam as a power monitoring device. A tilt angle of 20° is arbitrarily chosen as a compromise. The larger the angle, the easier it is for photodiode access and space for fiber connector. The smaller the angle, the easier to manufacture without edge chips and the more robust the overall unit. Optically, coatings can minimize the reflection for just about any angle, but for steep angles of incidence, there can be a great difference in the reflection coefficients for the two orthogonal polarizations. It's best to keep the difference small and use near-normal incidence angles.

Projection Lens

To project the object of square-faced emitter to the region of interest about 30 cm away, a simple two-element air-spaced condenser lens is used. Since we want to create an illuminated region of 76.2×76.2 mm from a 6.35×6.35 mm emitter, we need a magnification of 12.0×. This defines the ratio of image to object distance. For 320 mm (allowing some mechanical clearance for packaging), the required object distance is 26.7 mm. This corresponds to using a lens with a focal length of about 25 mm. The positional tolerance here is approximately ±0.5 mm.

Power Monitor

A photodiode and preamp circuit is included in the illumination subsystem to monitor the power being transmitted to the patient. The photodiode will be observing a small amount of light reflecting from the input face of the light guide. Without an anti-reflective coating, we expect about 4% of the total to be reflected, the usual Fresnel reflection, valid for small angles. To accommodate the reflected light, either the input face will be tilted slightly with respect to the axis of the light guide, or the fiber output will couple to the input face at a shallow angle.

The Fresnel reflections at both exit and entry faces can be either measured or calculated. The transmission of the condenser lens can be either measured or calculated. These characteristics that affect the total power delivered to the patient are quantities which do not change in time. It is a simple matter to generate a linear equation of power delivered to patient versus monitor photocurrent.

Detection Subsystem, Emission Filters

The infrared light from the laser at 806 nm excites fluorescence indocyanine green, which has been injected into the subject's bloodstream. The dye emits fluorescence at a peak wavelength of 830 nm. An emission filter is used to block the scattered laser light and pass the fluorescent light. Hence the filter is a bandpass filter.

The bandpass filter characteristics are a pass band centered at 830±5 nm and a 10 nm FWHM. It has a minimum attenuation in the stop band of OD 4.

The filter blocks the excitation laser light and the ambient light too. Hence, the device may be used in a brightly illuminated operating room.

Imaging Lens

The imaging lens is a commercial quality photographic lens with a male C-mount thread for attachment to the flange on the camera. The speed should be as fast as possible to collect the fluorescent light with the greatest efficiency. An initial specification is one which is commonly available in a variety of focal lengths—f/1.4. The CCD camera contains a CCD image sensor which is 6.45×4.84 mm (½ inch format). With a 16 mm focal length lens (commonly available focal length), the sensor "sees" a field of 122×92 mm, just over the required 75×75 mm.

CCD Camera

The CCD camera used is a commercially available unit from Hitachi. The KP-M2R has a spectral response that peaks at 640 nm and is useful in the NIR. Electrical power requirement is 12 VDC at 180 mA. Video output is via RS-170 on a standard BNC mount.

Specification of Laser Class.

To determine the laser class, use 21 CFR 1040.10 as the governing document. We start with a nominal 3 W laser output from the square 6.35×6.35 mm emitter. This radiation is inaccessible during normal operation. It passes through a projection lens to be focused to an image about 300 mm away. It is accessible during normal operation immediately after this lens.

The power through an aperture needs to be known to determine laser class. This will be accomplished by estimating the radiance of the final emitting surface (outer projection lens surface) and calculating the radiant transfer integral. The final surface of the light guide, while not truly diffuse, nonetheless approximates a uniformly emitting area; i.e. the power per small unit area is constant over the area of the emitter. Additionally, the emission is bounded in angle space; very little light is emitted at an angle greater than 8.6° (corresponding to the input fiber NA of 0.15).

A good approximation to the radiance (power per unit area per steradian) can be calculated this way. The total power from the fiber endface is 3 W. There will be approximately the same amount at the final condenser lens surface, assuming the use of good AR coatings on all surfaces. The area covered by the light on the final condenser surface is a square of about 13 mm on a side. Since the spacing from the light guide endface to the final condenser surface is 33.6 mm, simple geometry would give 16.5 mm using the 8.6° emission angle. The refraction at the first lens in the condenser makes this a bit smaller. A ZEMAX™ ray-trace calculation which includes the full refractive effects of all lens surfaces yields 13 mm. The emitting area is 1.69 cm². Since this lens projects an image 75×75 mm at 300 mm away, the new maximum emission angle is 5.9°, corresponding to a new solid angle of $33.3 \times 10^{-3}$ sr. Dividing the power by the area and the solid angle gives L=53.3 W/cm² sr.

The radiant transfer of power $\Phi$ from a source (subscript s) to a detector (subscript d) is $$\Phi = \int\int \frac{L\cos\theta_s \cos\theta_d}{s_{sd}^2} dA_s dA_d$$

where $\theta$ is the angle from the surface normal and s is the distance between the source and detector. The integrals are over the areas of the source and detector. The integral can be performed under the constraint of a circular source and a circular detector, the centers of which are both on axis. The result is $$\Phi = \frac{2L(\pi r_s r_d)^2}{r_s^2 + r_d^2 + s_{sd}^2 + \sqrt{(r_s^2 + r_d^2 + s_{sd}^2)^2 - 4r_s^2 + r_d^2}}$$

In this case, the specification calls for $r_d$=0.35 cm (corresponding to a 7 mm diameter aperture) and $s_{sd}$=20 cm (to maintain the $10^{-3}$ sr solid acceptance angle). The source radius is 0.65 cm. Since $s_{sd}$ is much bigger than either $r_s$ or $r_d$, we may approximate the result as $$\Phi = \frac{L(\pi r_s r_d)^2}{s_{sd}^2}$$

Evaluating this expression numerically gives 68.1 mW at the detector. A bit of a subtlety in the previous calculation is that the source radius is 0.65 cm. But the emitting area is closer to a square with side of 1.3 cm. However, the approximation is good since the corners of the square are much less bright than the center. The true illumination pattern away from the exit face of the light guide is more cross-shaped than square. This laser illumination system falls well within Class IIIb specifications.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A computer implemented method of intra-operatively confirming the removal of at least one vessel comprising an arteriovenous malformation in a subject, comprising:
    a. administering a fluorescent dye to a recipient subject;
    b. applying a sufficient amount of energy to a vessel in the subject such that the fluorescent dye fluoresces;
    c. detecting pixel data in a detection area to be imaged;
    d. transmitting the pixel data to a processor;
    e. obtaining a fluorescing image of the vessel;
    f. observing the fluorescing image to identify a location of an arteriovenous malformation;
    g. surgically removing the vessel including the arteriovenous malformation;
    h. intraoperatively confirming the removal of the vessel including the arteriovenous malformation by observing the fluorescing image to determine if a fluorescent signal stops at a point of removal of the vessel, wherein a lack of a fluorescent signal downstream of the point of removal indicates the arteriovenous malformation has been removed; and
    i. calculating on the processor a relative maximum fluorescent intensity in an area of fluorescence, the area of fluorescence indicated by a number of pixels associated with the fluorescing dye in a pre treatment image and a post treatment image corresponding to the detection area, wherein a fewer number of pixels and less fluorescent intensity at the detector area indicates a removal of the arteriovenous malformation, and a greater number of pixels and greater fluorescent intensity at the detection area indicates a non-removal of the arteriovenous malformation.

2. The method of claim 1, wherein the recipient subject is an animal.

3. The method of claim 1, wherein the animal is a human.

4. The method of claim 1, wherein the fluorescent dye is a tricarbocyanine dye or an analog thereof.

5. The method of claim 4, wherein the tricarbocyanine dye is indocyanine green.

6. The method of claim 1, wherein the fluorescent dye comprises a mixture or combination of multiple fluorescent dyes or analogs thereof.

7. The method of claim 1, wherein the dye is administered intravenously.

8. The method of claim 1, wherein the dye is administered by catheter or cannula.

9. The method of claim 1, wherein the dye is administered as a bolus injection.

10. The method of claim 1, wherein the dye is administered less than an hour before confirming removal of the arteriovenous malformation.

11. The method of claim 1, wherein the dye is administered more than 30 seconds confirming removal of the arteriovenous malformation.

12. The method of claim 1, wherein the energy is light energy.

13. The method of claim 12, wherein the light energy is provided by a laser.

14. The method of claim 13, wherein the laser power output is about 2.5 watts.

15. The method of claim 14, wherein the laser power output lasts for about 30 seconds.

16. The method of claim 14, wherein the output is a continuous wave.

17. The method of claim 12, wherein the light energy is provided by an incandescent light and a filter.

18. The method of claim 12, wherein the wavelength of the light energy is in the infra-red spectrum.

19. The method of claim 12, wherein the wavelength of the light energy is about 805 nanometers.

20. The method of claim 1, wherein the image is obtained by a camera.

21. The method of claim 20, wherein the camera is a charge coupled device.

22. The method of claim 20, wherein the camera is a video recorder.

23. The method of claim 1, wherein the vessel is a blood vessel.

24. The method of claim 1, wherein the vessel is an artery.

25. The method of claim 1, wherein the vessel is a vein.

26. The method of claim 1, wherein the vessel is a nidus associated with AVM.

27. The method of claim 1, wherein the vessel is surgically exposed.

28. A computer implemented method of intra-operatively locating at least one vessel comprising an arteriovenous malformation in a subject, comprising:
  a. administering a fluorescent dye to a recipient subject;
  b. applying a sufficient amount of energy to at least one vessel to the subject such that the fluorescent dye fluoresces;
  c. detecting pixel datain a detection area to be imaged;
  d. transmitting the pixel data to a processor;
  e. obtaining a fluorescing image of the at least one vessel;
  f. intraoperatively locating a suspect vessel of said at least one vessel, the suspect vessel having an arteriovenous malformation;
  g. observing the image to determine if the fluorescent signal leaks from the suspected vessel, wherein a leak of a fluorescent signal from the suspected vessel indicates an arteriovenous malformation; and
  h. calculating on the processor a relative maximum fluorescent intensity in an area of fluorescence, the area of fluorescence indicated by a number of pixels associated with the fluorescing dye in a pre treatment image and a post treatment image corresponding to the detection area, wherein a fewer number of pixels and less fluorescent intensity at the detector area indicates a removal of the arteriovenous malformation, and a greater number of pixels and greater fluorescent intensity at the detection area indicates a non-removal of the arteriovenous malformation.

29. The method of claim 28, wherein the recipient subject is an animal.

30. The method of claim 29, wherein the animal is a human.

31. The method of claim 28, wherein the fluorescent dye is a tricarbocyanine dye or an analog thereof.

32. The method of claim 31, wherein the fluorescent dye comprises a mixture or combination of a first fluorescent dye or analogs thereof and a second fluorescent dye or analog thereof.

33. The method of claim 31, wherein the tricarbocyanine dye is indocyanine green.

34. The method of claim 28, wherein the dye is administered intravenously.

35. The method of claim 28, wherein the dye is administered as a bolus injection.

36. The method of claim 28, wherein the dye is administered by catheter or annula.

37. The method of claim 28, wherein the dye is administered less than an hour before confirming removal of the arteriovenous malformation.

38. The method of claim 28, wherein the dye is administered more than 30 seconds confirming removal of the arteriovenous malformation.

39. The method of claim 28, wherein the energy is light energy.

40. The method of claim 39, wherein the light energy is provided by a laser.

41. The method of claim 40, wherein the laser power output is about 2.5 watts.

42. The method of claim 41, wherein output is a continuous wave.

43. The method of claim 40, wherein the laser power output lasts for about 30 seconds.

44. The method of claim 39, wherein the light energy is provided by an incandescent light and a filter.

45. The method of claim 39, wherein the wavelength of the light energy is in the infra-red spectrum.

46. The method of claim 39, wherein the wavelength of the light energy is about 805 nanometers.

47. The method of claim 28, wherein the image is obtained by a camera.

48. The method of claim 47, wherein the camera is a charge coupled device.

49. The method of claim 47, wherein the camera is a video recorder.

50. The method of claim 28, wherein the vessel is a blood vessel.

51. The method of claim 28, wherein the vessel is an artery.

52. The method of claim 28, wherein the vessel is a vein.

53. The method of claim 28, wherein the vessel is a nidus associated with AVM.

54. The method of claim 28, wherein the vessel is surgically exposed.

55. A portable system comprising:
  a) a device for administering fluorescent dye to a subject;
  b) an energy source capable of emitting two laser beams of sufficient energy such that the fluorescent dye fluoresces;
  c) an imaging head for imaging at least one vessel; and
  d) a processor coupled to perform the method of claim 1 or claim 28.

56. The system of claim 55, comprising a field of view having a first dimension of about 0.5 to 1.5 inches and a second dimension of about 0.5 to about 1.5 inches.

57. The system of claim 55, wherein the first and second dimension are approximately 1 inch.

58. The system of claim 55, wherein the system has an irradiance in the range of about 15-25 mW/cm$^2$.

59. The system of claim 55, wherein the two laser beams converge at a common focal point.

60. The system of claim 55, wherein the two laser beams comprise green light.

61. The system of claim 55, wherein the two laser beams comprise radiation in the infrared spectrum.

62. The system of claim 55, said system comprising a second energy source capable of emitting sufficient energy to excite a second fluorescent dye such that said second fluorescent dye fluoresces.

63. The system of claim 55, wherein the imaging head is contained in an endoscope.

64. The system of claim 55, wherein the imaging head is contained in a surgical microscope.

* * * * *